(12) United States Patent
Komeh-Nkrumah

(10) Patent No.: US 8,821,948 B2
(45) Date of Patent: Sep. 2, 2014

(54) THERAPEUTIC, BIO-AFFECTING AND BODY TREATING COMPOSITION

(76) Inventor: Steva A. Komeh-Nkrumah, Baltimore, MD (US)

( * ) Notice: Subject to any disclaimer, the term of this patent is extended or adjusted under 35 U.S.C. 154(b) by 0 days.

(21) Appl. No.: 13/040,619

(22) Filed: Mar. 4, 2011

(65) Prior Publication Data

US 2011/0217395 A1 Sep. 8, 2011

Related U.S. Application Data

(60) Provisional application No. 61/339,523, filed on Mar. 4, 2010.

(51) Int. Cl.
*A61K 36/67* (2006.01)

(52) U.S. Cl.
USPC .......................................................... 424/734

(58) Field of Classification Search
None
See application file for complete search history.

(56) References Cited

U.S. PATENT DOCUMENTS

| | | | |
|---|---|---|---|
| 6,280,751 B1 | 8/2001 | Fletcher et al. | |
| 6,340,480 B1 | 1/2002 | Duckett et al. | |
| 6,342,253 B1 | 1/2002 | Whitledge | |
| 6,582,736 B2 | 6/2003 | Quezada | |
| 7,348,034 B2 | 3/2008 | Murray et al. | |
| 7,531,194 B2 | 5/2009 | Wu et al. | |
| 2006/0105055 A1* | 5/2006 | Marenick et al. | 424/581 |
| 2007/0031367 A1* | 2/2007 | Brown et al. | 424/74 |

FOREIGN PATENT DOCUMENTS

| | | | |
|---|---|---|---|
| BE | 1011858 A7 * | 2/2000 | |
| CH | 678487 A * | 9/1991 | |
| FR | 84159 E * | 12/1964 | |
| FR | 2794973 A1 * | 12/2000 | |
| FR | 2845594 A1 * | 4/2004 | |
| KR | 2001078904 A * | 8/2001 | |
| KR | 2003074511 A * | 9/2003 | |

* cited by examiner

*Primary Examiner* — Amy L Clark
(74) *Attorney, Agent, or Firm* — Larry J. Guffey

(57) ABSTRACT

A medicinal composition comprising an apportioned combination of at least eight essential oils selected from the group consisting of *calophyllum inophyllum, citrus aurantium, eucalyptus globulublus, eugenia caryophyllata, foeniculum vulgare, helichrysum angustifolia, juniperus virginiana, lavendula officinalis, muristica fragrans, ocimum basilicim, pinus sylvestrius, piper nigrum, rosemarinus officinalis, salvia officinalis lamiacae, salvia sclarea* and *zingiber officinale*. When configured for topical dermal application, this composition has been shown to be therapeutically effective at relieving pain.

6 Claims, 1 Drawing Sheet

|   | Essential Oils | Proportions of Essential Oil In Most Tested Composition |
|---|---|---|
| 1 | Ocimum basilicim (basil) | 2 |
| 2 | Citrus aurantium (bitter orange) | 2 |
| 3 | Piper nigrum (black pepper) | 2 |
| 4 | Salvia sclarea (clary sage) | 2 |
| 5 | Juniperus virginiana (cedarwood) | 0.5 |
| 6 | Eugenia caryophyllata (clove bud) | 2 |
| 7 | Eucalyptus globulublus (eucalyptus) | 1 |
| 8 | Calophyllum inophyllum (foraha) | 1 |
| 9 | Foeniculum vulgare (fennel) | 1 |
| 10 | Zingiber officinale (ginger) | 2 |
| 11 | Helichrysum angustifolia (immortel) | 1 |
| 12 | Lavendula officinalis (lavender) | 1 |
| 13 | Muristica Fragrans (nutmeg) | 2 |
| 14 | Pinus sylvestrius (pine needle) | 1 |
| 15 | Rosemarinus officinalis (rosemary) | 1 |
| 16 | Salvia officinalis lamiacae (sage) | 1 |

Oil Mixture contains: 20% essential oils, 70% carrier oil and 10 % stabilizer

THERAPEUTIC, BIO-AFFECTING AND BODY TREATING COMPOSITION

CROSS-REFERENCE TO RELATED APPLICATION

This application claims the benefit of Provisional Patent Application No. 61/339,523, filed Mar. 4, 2010 by Steva A. Komeh-Nkrumah. The teachings of this application are incorporated herein by reference to the extent that they do not conflict with the teaching herein.

BACKGROUND OF THE INVENTION

1. Field of the Invention

This invention relates to bio-affecting and body treating compositions. More particularly, this invention relates to a therapeutic composition or balm consisting of specific essential oils.

2. Description of the Related Art

For thousands of years, many cultures of humanity have looked across their world and sought remedies to relieve pain. From the four corners of this planet they have developed therapeutic medicines from the very plants, trees, flowers and even the roots themselves. In the days of ancient Egypt, Papyrus manuscripts dating back 2800 BC recorded the use of hundreds of medicinal herbs, fine oils and perfumes. The Egyptians held many of these essential oils in high regard due to their therapeutic properties. When the Greeks visited Egypt, they learned a great deal regarding the medicinal applications of aromatic plants. The father of medicine, Hippocrates, prescribed fumigations and fomentations. Megallus himself created a famous preparation, made from myrrh, cinnamon and cassis. This was used both as a perfume and as a remedy for skin inflammation and battle wounds.

Plants and herbs have long been used for medicinal purposes. Indeed, Native Americans have long known of the healing powers of certain herbs as remedies for various illnesses. Well known examples of using plants and herbs for medicinal purposes include aspirin, which comes from the bark of a white willow tree, and digitalis, which comes from a flower commonly known as Foxglove.

The Arabs produced many great men of science, among them Avicenna (980-1037 AD). Of his many fine works and discoveries, he invented the refrigerated coil, a breakthrough in the art of distillation, which he used to produce essential oils. During these times, there was an outlook possessed by these inventors, a common interest in the interrelatedness of matter and spirit. They used their intuition with the known sciences of their day.

As the Renaissance period came and went, so did the role of essential oils for direct therapeutic intervention. With the arrival of technical chemistry, synthetic counterparts of essential oils created the modern drug industry. They reduced the role of essential oils to employment in perfumes, cosmetics and foods.

In these modern times, pain management is of great concern for those who are prescribed various drugs. Side effects and toxicity are very real experiences mounting negative evidence of these synthetic versions. Accordingly, there is a need for a natural oil composition which can be used for physical therapy in treating human body pains, including rheumatoid arthritis (RA).

Rheumatoid arthritis is an autoimmune disease of high prevalence rate in the United States and several other countries. Rheumatoid arthritis is a leading cause of disability, and it adversely affects the quality of life. The drugs that are currently prescribed to treat rheumatoid arthritis are expensive and often cause adverse health effects. Therefore, safer and less expensive alternative therapeutic products are increasingly being sought.

In this regard, a variety of compounds that might be of potential use as drugs for the treatment of rheumatoid arthritis and other chronic inflammatory conditions are continually being evaluated. Animal testing is often a key part of these evaluations. For example, the injection of adjuvant (*Mycobacterium butyricum* suspended in mineral oil) into rats produces an immune reaction that characteristically involves inflammatory destruction of cartilage and bone of the distal joints with concomitant swelling of surrounding tissues. Rats with such induced arthritis (i.e., adjuvant-induced arthritis (AA)) are then used to evaluate various test compounds for their ability to inhibit the adjuvant-induced arthritis' inflammatory response.

Several compound evaluation studies have shown that some rheumatoid arthritis-like symptoms can be significantly ameliorated in rats with adjuvant-induced arthritis. For example, studies suggesting the efficacy of topical application of various compounds include: the anti-inflammatory activity of Boswellic acids and ginkgetin and biflavonoid mixtures, and relief from the symptoms of arthritis suggested by the use of essential oils from ginger, orange and black cumin.

Despite these promising results and the existence in the marketplace of many medicinal pain relievers, there continues to be a need for the discovery and development of new and improved pain relief methods and products.

SUMMARY OF THE INVENTION

Recognizing the need for more effective natural oil compositions which can be used for physical therapy in treating pain, especially arthritis pain, the present invention is generally directed to satisfying this need.

In accordance with the present invention, such a therapeutic composition includes an apportioned combination of at least eight essential oils selected from the group consisting of *calophyllum inophyllum, citrus aurantium, eucalyptus globulublus, eugenia caryophyllata, foeniculum vulgare, helichrysum angustifolia, juniperus virginiana, lavendula officinalis, muristica fragrans, ocimum basilicim, pinus sylvestrius, piper nigrum, rosemarinus officinalis, salvia officinalis lamiacae, salvia sclarea* and *zingiber officinale*.

The selected essential oils will usually have a weight percentage in this medicinal composition that is in the range of 10% to 40%. The balance of the composition will be a stabilizer having a weight percentage in the composition of approximately 10%, and a carrier oil which has a weight percentage in the range of 50% to 80%.

When configured for topical dermal applications, this composition has been shown to be therapeutically effective at relieving arthritic pains.

Thus, there has been broadly summarized above, and understanding that there are other preferred embodiments which have not been summarized above, the present invention in order that the detailed description that follows may be better understood and appreciated. There are, of course, additional features of the invention that will be described hereinafter and which will form the subject matter of the later presented claims to the present invention.

BRIEF DESCRIPTION OF THE DRAWINGS

FIG. 1 shows the apportionment of the 16 essential oils of the present invention that have undergone both animal and human testing.

DESCRIPTION OF THE PREFERRED EMBODIMENT

Before explaining at least one embodiment of the present invention in detail, it is to be understood that the invention is not limited in its application to the details of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The term "treatment" or "treating," as used herein, refers to improving conditions.

The term "patient," as used herein, refers to animals, especially mammals. In a preferred embodiment, the patient is human.

The term "therapeutically effective amount," as used herein, refers to the amount of components of the pharmaceutical composition of the invention alone or in combination with other medicaments that could provide therapeutic benefits in treatment.

The term "carrier oil," as used herein, refers to diluents and acceptable agents or the like that are well known by those of ordinary skill in the art and can be used in the preparation of medicinal compositions.

The term "essential oils (EO)," as used herein, are natural plant products that possess anti-oxidant, anti-bacterial, anti-fungal and anti-inflammatory properties.

The properties of the eight to sixteen essential oils used in the present invention are given below. The source of this information is Camden-Grey Essential Oils, Inc., 3579 NW 82 Ave., Doral, Fla. 33122 (U.S.A.) and their comments regarding their oils include:

1. Basil *Ocimum basilicum*, steam distilled herb, India. Our basil EO has contents of 70-72% of methyl cavicol and 15-18% of linalool. Described as warm, spicy and herbal, with a hot, somewhat anise tasting "bite." Generally used as an antispasmodic, anti-inflammatory, pain reliever, decongestant of the veins, antibacterial. Basil is an addition to many perfume blends, it reportedly works as a brain and memory stimulant and soothes stress, depression, and mental fatigue. Blended with Rosemary verbenon, it reportedly makes an excellent blend to be used as an external application on the hair and scalp to stimulate growth and condition the hair. Basil is also indicated for urinary infections, rheumatoid arthritis and insufficient digestive enzymes. Good for tired, overworked muscles, as a mouthwash for mouth sores and infected gums, for chest infections and digestive problems. It blends well with bergamot, lavender, neroli and verbena. Flash point: 167° F.

2. Black pepper essential oil (1 oz.) Pepper, Black: *Piper nigrum*, steam distilled peppercorn/berry, India (standard cultivation). This EO has a fresh, dry-woody, warm and spicy scent. It's analgesic, antiseptic, antispasmodic, aphrodisiac, diuretic, laxative and stomachic. There's the possibility of skin irritation. Black pepper is very stimulating to the mind, gives stamina where there's frustration. Its rubefacient and analgesic properties make it useful for muscular aches and pains and muscular stiffness as it assists with dilation of local blood vessels. Its stomachic effect increases flow of saliva and stimulates appetite, expels wind, encourages peristalsis and is useful in bowel problems; restores tone to colon muscles. It blends well with basil, bergamot, cypress, grapefruit, lemon, and sandalwood. Flash point: 180° F.

3. Clary Sage—*Salvia sclarea*—steam distilled flower/leaf—Russia. Its scent is fruity, floral, herbaceous, nutty and heavy. This is a relaxing, warming oil which eases nervous tension. Known as a hormone balancer, it may regulate scanty periods. Its well known for its euphoric action and is an extremely valuable oil for treating nervousness, fear, paranoia and depression. Its antispasmodic and emmenagogue properties make it useful for helping with uterine problems such as easing PMS, regulating scanty periods and easing painful cramps in the lower back. Also encourages labor, enabling the expectant mother to relax and eases post-natal depression. Studies have found Clary Sage to be beneficial for its analgesic and relaxing effects and its ability to accelerate labor. It inhibits prolactin which tends to dry up breast milk. It reportedly soothes digestive problems. Not to be used during pregnancy! It blends well with bergamot, lavender, lime, and geranium. Flash point: 125° F. (Cannot ship via air or ocean w/o appropriate documentation, cannot ship via postal air services.)

4. Cedarwood—*Juniperus virginiana*—steam distilled wood—U.S.A. Also known as Red cedar, it is from the family Cupressace. Although this tree is from this family and not from the family Pinace, it is still called Virginia Cedar. Its scent is sweet and woody, sometimes reminiscent of sandalwood. It reportedly calms nervous tension and states of anxiety. It is an expectorant and dries phlegm. It is recommended for hemorrhoids. It deters moths and other insects, usually in drawers and closets. Care should be taken that garments do not directly touch wood treated with Cedarwood essential oil. It blends well with bergamot, cinnamon, frankincense, rose, sandalwood and rosemary. Flash point: 200° F.

5. Clove: *Eugenia caryophyllata*—clove bud steam distilled, organic—Madagascar. Clove oil has a sweet, rich, warm, spicy and penetrating aroma with a fruity top note and a woody base note. Highly irritant to the skin, must be diluted, clove bud oil is safer to use than clove leaf due to its lower eugenol content. It should never be used directly on the skin or in large concentrations. Clove oil lifts depression and is recommended as an inhalation when feeling weak and lethargic. It's excellent as an antiseptic because of the high proportion of eugenol. It helps stimulate digestion, restores appetite and relieves flatulence. The dental value of cloves is well know, the oil has been traditionally used to relieve toothaches. Clove oil is not used in skin care except to treat infectious wounds, skin sores and leg ulcers. It is reportedly beneficial to the digestive system, effective against diarrhea, vomiting and spasms. Can help toothache, rheumatism, arthritis and mouth sores. It blends well with basil, cinnamon, citronella, orange and peppermint. Flash point: 200° F.

6. Eucalyptus, the Thymes type: Nice, strong, true scent. Smells absolutely like essential oils . . . very natural!!! You can really smell the top notes (the menthol) of the eucalyptus here—it smells very genuine and clean. Scent is invigorating, but pleasant. The aroma is rich and clean of eucalyptus with camphor, pine, and floral notes. It's a "green" smell . . . not medicinal. Flashpoint: 160° F.

7. Faraha (a/k/a tamanu, kamanu and Alexandrian laurel) *Calophyllum Inophyllum*, organic. This cold pressed oil is rich and thick, with a delicate nutty or honey-spice aroma. The color of this oil will vary from vendor to vendor, we have offered very dark green Foraha and we have offered Foraha of an amber color. It stimulates cell regeneration and is good for fragile or broken capillaries. Foraha is a traditional medicine in the South Pacific, where it is used for its analgesic antiinflammatory and cicatrizant properties. Formerly, foraha was used to treat leprosy. It helps wounds to heal and is soothing for eczema and skin irritations such as burns, rashes and insect bites. It is used as an aid for relieving pain, healing wounds, herpes lesions and post-surgical scars. A combination of foraha and Ravensara aromatica essential oil has been used successfully as a treatment for shingles. Rarely used as a carrier oil due to its quite thick in consistency, but may be part of a blend with other carrier oils. It's highly recommended as a facial oil, either alone or with essential oils added.

8. Fennel—*Foeniculum vulgaris*—steam distilled seed—Spain. It has a sweet, aniseed-like aroma. It is reportedly an antiseptic, diuretic, expectorant, insecticide and laxative. Its main qualities are warming and drying. It is an excellent body cleanser, may rid the system of toxins from alcohol and excessive eating, great for hangovers. It may be used for the treatment of cellulite when accumulations of toxic wastes and fluids in the subcutaneous fat produce a characteristic wrinkled appearance. Also used for the lungs as an antispasmodic and expectorant. It may be used in treating cold conditions and bronchitis. It decreases appetite. It blends well with lavender, lemon, rose, and sandalwood. Flash point: 145° F.

9. Ginger—*Zingiber officinale*—steam distilled root—China. Its smell is described as spicy, woody, warm, with a hint of lemon and pepper. It is antiseptic, analgesic, expectorant, laxative, and aphrodisiac. Reportedly, it aids memory, eases sore throats, settles the digestive system, and is effective against nausea, hangovers, jet lag, sea and travel sickness. It blends well with cajeput, cinnamon, eucalyptus, frankincense, geranium, orange and verbena. Flash point: 130° F.

10. Helichrysum (a/k/a Everlasting, Immortelle)—*Helichrysum italicum*—steam distilled flowering top—Corsica (organic). An intense rich aroma with a herbaceous note. Among its properties are anti-inflammatory, antimicrobial, antitussive, astringent, diuretic, expectorant, fungicidal and cicatrisant. The French used this oil primarily as an anti-inflammatory to regulate cholesterol, stimulate the cells of the liver, and as an antispasmodic. This particular variety has powerful antibruise properties. It's ideal to use in lymphatic drainage massage, acts as a stimulant for the liver, gall bladder, kidneys and spleen—the organs responsible for detoxifying the body. Italidone, one of its chemical components, has been found to have strong mucous thinning, expectorant and cicatrisant properties. It blend well with bergamot, chamomile, geranium, orange and frankincense. Flash point: 124° F.

11. Lavender—*Lavandula officinalis*—steam distilled flowering top—France. Lavender's aroma is floral, herbaceous, light with woody undertones. Among its many properties, it's known to be analgesic, antidepressant, antirheumatic, antiseptic, antispasmodic, antiviral, bactericide, cicatrizant, decongestant, deodorant, diuretic, fungicide, sedative. It reportedly soothes the spirit and relieves anger. Has a sedative action on the heart, assists in bringing down high blood pressure, relieves insomnia, relieves muscular spasms and rheumatic pains. The first essential oil one should reach for in the case of minor burns and sunburn. Useful with menstrual problems, bronchitis and headaches, helps lower blood pressure. Lavender is one of the safest essential oils to use with children and the elderly. It blends well with bergamot, chamomile, citronella, lemon, and pine. Flash point: 156F.

12. Neroli *Citrus aurantium* ssp. *aurantium*, (aka bitter orange)—steam distilled fresh flower—Tunisia. There are two types of orange tree, the sweet orange and the bitter orange. Oil from orange blossoms is known as neroli oil and is extracted from the white blossoms of the bitter orange. It has a powerful, but delicate bitter-sweet floral fragrance. Neroli essential oil is antidepressant, antiseptic, antispasmodic, deodorant, digestive, stimulant and sedative. Good in cases of insomnia, best used in the bath before bedtime. Due to its antispasmodic action, Neroli is well known for its ability to relieve muscle spasm of the smooth muscles, especially that of the small intestines. It is extremely useful for chronic diarrhea, especially when this arises from nervous tension. This oil is suitable for all skin types since it does not irritate and is also useful for the treatment of broken capillaries under the skin's surface. It blends well with bergamot, geranium, jasmine, lavender, lime, rose and ylang ylang. Flash point: 158° F.

13. Nutmeg—*Myristica fragrans*—steam distilled dried seed—Indonesia (also known as East Indian nutmeg). It has a spicy, warm and sweet odor. It is considered analgesic, antiseptic, antispasmodic, emmenagogue, parturient, and tonic. It is used in massage blends for aching joints because of its warming property. Inhaling it may cause nausea. It blends well with citrus oils. Flash point: 109° F.

14. Pine needle—It has a strong, dry-balsamic, turpentine like odor. It is antiseptic, bactericidal, decongestant, deodorant, diuretic, expectorant, and insecticidal. Known to refresh a tired mind and mental fatigue . . . it is invigorating. It is helpful in cases of bronchitis, laryngitis and influenza. It has a good effect on respiratory problems due to its expectorant properties. Its warming properties may relieve rheumatism, gout and arthritis, may be beneficial for muscular pain and stiffness. It is a wonderful house cleaner and deodorizer. It blends well with cedarwood, clove, myrtle, and niaouli. Pine can be very irritating on the skin, use with caution. Flash point: 107° F.

15. Rosmary—It has a strong, clear, penetrating, camphoraceous and herbaceous aroma. It is analgesic, antidepressant, antirheumatic, antiseptic, antispasmodic, astringent, cicatrisant, digestive, diuretic, hypertensive and rubefacient. Not suitable for people with epilepsy or high blood pressure. Avoid in pregnancy since it is an emmenagogue. It reportedly aids memory, helps ease gout and tired, overworked muscles. Since it stimulates blood circulation, it is a good remedy for low blood pressure. It's used in shampoo and hair treatments, it helps stimulate blood circulation to the scalp, thus being beneficial for promoting hair growth. It blends well with basil, cedarwood, frankincense, ginger, grapefruit, orange and peppermint. Flash point: 104° F.

16. Sage Dalmatian is one of several species of sage. Its aroma is clear, herbal, camphorous and sharp. Traditionally, sage has been used for a variety of disorders such as respiratory infections, menstrual difficulties, and digestive complaints. Apart from its widespread use in cooking, sage has always been used in herbal infusions, gargles, vinegars and poultices, particularly for mouth and throat infections. An essential oil, its properties are anti-inflammatory, antibacterial, antiseptic, digestive and diuretic. This oil blends well with bergamot, eucalyptus, orange, peppermint, and rosemary. Should be used with caution, avoid with people with epilepsy or high blood pressure, do not use in children or the elderly, avoid in pregnancy as it's an abortifacient. Sage contains thujone, a substance which is considered toxic in high doses. Flash point: 125F.

From observing these vendor comments, it can be noted that the reported beneficial properties of these oils are such that a beneficial property such as "anti-inflammatory" cannot be attributed to only a single of these essential oils. Much testing is still need to confirm the magnitude of most of these reported beneficial properties. How these beneficial properties are impacted by mixing together these essential oils are generally unknown.

For pain relief purposes, it is my hypothesis that a blend of these essential oils will have beneficial properties that will significantly exceed that which can be achieved by any one essential oil. I believe this to be the case since I consider the causes of muscular aches and pains to come from many possible divergent sources, and I believe that using an assortment of essential oils for pain relief provides one with many different possible ways to address the causes of pain and increases the chances for achieving pain relief when a single ointment is applied to many different complaints from and descriptions of pain.

I call it the choral concept of therapy. In a chorus you have many people singing the same song together. They have different tonal qualities but they are grouped together as soprano, alto, bass, etc. In my combinations of essential oils, the constituent essential oils can be grouped as anti-inflammatory, analgesic, anti-rheumatic, antibacterial, etc. Each constituent group delivers its own beneficial property in its own way, and together my combinations of essentials oils accomplish what no single essential oil can accomplish.

The present invention is characterized by the use of various proportions of essential oils for treating human body pains. Thus, the invention provides a natural or medicinal composition for relieving a user's physical aches and pains.

For example, a first embodiment of the present invention is seen to be a mixture of 70% carrier oil, 20% of appropriately proportioned eight to sixteen essential oils, and 10% stabilizer.

The most suitable route and application methods for treatment will be easily determined by those skilled in the art. According to the invention, the preferred route is a topical dermal application. Dosage will depend on the nature and states of the symptoms being treated, ages and general physical conditions of the patient being treated, application methods and any therapies practiced previously.

It should be understood by those skilled in the art that the dosage will vary with patients, depending on age, size, health condition, and related factors. Furthermore, if desired, the composition could be sterilized, or mixed with any pharmaceutically acceptable carrier and stabilizers. The preparation of the essential oil combinations or ointments described herein can be performed by those skilled in the art according to conventional methods.

In preferred embodiments of the present invention, the preparation of an essential oil ointment for topical dermal delivery was as follows. Essential oils and bees wax (BW) were purchased from Camden-Grey Essential Oils Inc. (Doral, Fla.), and corn Oil (CO) was purchased from a local supermarket. CO was used as the carrier oil for the essential oils, whereas BW was used as the base to prepare a semi-solid ointment of essential oils and CO. BW and carrier oil were heated together until thoroughly combined and then removed from the heat source. The blend of anti-inflammatory and analgesic essential oils was added to the carrier oil-BW mixture, covered and mixed thoroughly by vortexing. The resulting ointment was allowed to cool. Experimental ointments were prepared using the desired concentrations of 8-16 essential oils.

The present invention is described in detail with reference to the following non-limiting example. Any modifications and changes that can be easily achieved by those skilled in the art are included in the scope of the disclosure of the specification and appended claims.

The embodiment of the present invention that has been tested and evaluated the most is as follows: a mixture of 70% carrier oil, 20% essential oils, 10% stabilizer, where the appropriate proportions of the 16 essential oils used in this embodiment are:

2 parts *Ocimum basilicim*,
2 parts *Citrus aurantium*,
2 parts *Piper nigrum*,
2 parts *Salvia sclarea*,
0.5 part *Juniperus virginiana*,
2 parts *Eugenia caryophyllata*,
1 part *Eucalyptus globulublus*,
1 part *Calophyllum inophyllum*,
1 part *Foeniculum vulgare*,
2 parts *Zingiber officinale*,
1 part *Helichrysum angustifolia*,
1 part *Lavendula officinalis*,
2 parts *Muristica Fragrans*,
1 part *Pinus sylvestrius*,
1 part *Rosemarinus officinalis*,
1 part *Salvia officinalis lamiacae*; and
where the carrier oil includes: 1 part rose hip seed oil, 1 part black cumin seed oil and 1 part Arnica oil, and where the stabilizer includes: 1 part bees wax, 1 part Shea Butter and 1 part floral (Jasmine) wax. See FIG. 1.

The percentages of essentials oils in various tested ointments have been in the range of 10%-40%, with 10% stabilizers and the remainder (i.e., 50%-80%) of the ointment being a carrier oil.

Animal testing was used to examine the effect of this ointment containing essential oils (EO) on the severity of adjuvant arthritis (AA) in Lewis rats. At the onset of AA, rats received topical application twice daily of ointment containing 20% EO or placebo ointment and continued for a total of 7 days. Throughout the disease process, the severity of arthritis was graded on a scale of 0-10 (no severity—0, most sever—10) regularly. Rats treated with 20% EO showed a significantly reduced severity of AA compared to rats treated with ointment lacking EO. For the details of this research, see to-be-published paper entitled "Topical Dermal Application of Essential Oils Attenuates the Severity of Adjuvant Arthritis in Lewis Rats," Komeh-Nkrumah, Nanjundaiah, Rajaiah, Yu and Moudgil (2011).

For therapeutic purposes, EO can be administrated by three methods, absorption through the skin, inhalation and ingestion. Although I have attributed the beneficial anti-arthritic effect of EO to topical application, grouping animals in separate cages by treatment regimen was insufficient to prevent rats in the control and placebo groups from inhaling the volatile essential oils. Occasionally, I observed animals licking the ointment from their paws; however, benefits of ingesting or inhaling essential oils were not investigated in these animal tests. Nevertheless no adverse reactions of the rats to ingestion of the EO ointments were observed.

The present invention has undergone some limited human testing with very positive results and appears to be a viable alternative therapy for relief of pain and other afflictions. Examples of such tests and treatments are described below.

EXAMPLES OF TREATMENT 32 year old male who experienced painful sports injury to thigh muscle stated that "his pain was reduced within 3 hours" after topical application an ointment containing the apportionment of essential oils identified in FIG. 1 (hereinafter "TI ointment").

72 year old male, post knee replacement, refused his orthopedic surgeon recommendation for a second knee replacement after daily use of TI ointment for pain. He attributes daily use of the TI ointment and physical therapy for cessation of further deterioration of his knee.

55 year old woman who had hip replacement 5 years ago and was told that she would need to replace the other hip. After using TI ointment, she states that she does not anticipate having to replace the other hip in the near future.

80 year old man who has had one hip replaced and two painful knees states that pain is relieved after using TI ointment.

59 year old man who has had 2 surgical procedures on his back reports fewer flare ups and less stiffness after using TI ointment.

60 year old man was diagnosed with spinal stenosis, bone spurs, and cartilage damage. He was unable to stand up straight, to walk without a cane and was experiencing excruciating pain. A partial laminectomy was recommended. After two weeks using the TI ointment once per day, he is able to stand straight and to walk to work without the cane. He is able to do his prescribed exercises with less pain, to sleep better and no longer experiences numbness in his legs.

The information disclosed above is illustrative only of the principles of the invention. Further, since numerous modifications and changes will readily occur to those skilled in the art, and because of the wide extent of the teachings disclosed herein, the foregoing disclosure should not be considered to limit the invention to the exact compositions or apportionments of essential oils shown and described herein. Accordingly, all suitable modifications and equivalents of the present disclosure may be resorted to and still considered to fall within the scope of the invention as set forth in the claims to the present invention.

I claim:

1. A topical composition for treating muscular aches and pains in mammals comprising a therapeutically effective amount of: *Calophyllum inophyllum, Citrus aurantium, Eucalyptus globulus, Eugenia caryophyllata, Foeniculum vulgare, Helichrysum angustifolia, Juniperus virginiana, Lavendula officinalis, Myristica fragrans, Ocimum basilicim, Pinus sylvestris, Piper nigrum, Rosemarinus officinalis, Salvia officinalis lamiacae, Salvia sclarea* and *Zingiber officinale*.

2. The topical composition of claim 1, wherein said *Calophyllum inophyllum, Citrus aurantium, Eucalyptus globulus, Eugenia caryophyllata, Foeniculum vulgare, Helichrysum angustifolia, Juniperus virginiana, Lavendula officinalis, Myristica fragrans, Ocimum basilicim, Pinus sylvestris, Piper nigrum, Rosemarinus officinalis, Salvia officinalis lamiacae, Salvia sclarea* and *Zingiber officinale* are present in a combined total amount of 10% to 40 wt. % of said composition, and wherein said composition further comprises: a stabilizer in an amount of approximately 10 wt %, and a carrier oil in an amount of 50-80 wt.

3. The topical composition of claim 1, wherein said topical composition comprises *Calophyllum inophyllum* in an amount of 1 part, *Citrus aurantium* in an amount of 2 parts, *Eucalyptus globulus* in an amount of 1 part, *Eugenia caryophyllata* in an amount of 2 parts, *Foeniculum vulgare* in amount of 1 part, *Helichrysum angustifolia* in an amount of 1 part, *Juniperus virginiana* in an amount of 0.5 parts, *Lavendula officinalis* in an amount of 1 part, *Myristica fragrans* in an amount of 2 parts, *Ocimum basilicim* in amount of 2 parts, *Pinus sylvestris* in an amount of 1 part, *Piper nigrum* in an amount of 2 parts, *Rosemarinus officinalis* in an amount of 1 part, *Salvia officinalis lamiacae* in an amount of 1 part, *Salvia sclarea* in an amount of 2 parts and *Zingiber officinale* in an amount of 2 parts.

4. The topical composition of claim 2, wherein said topical composition comprises *Calophyllum inophyllum* in an amount of 1 part, *Citrus aurantium* in an amount of 2 parts, *Eucalyptus globulus* in an amount of 1 part, *Eugenia caryophyllata* in an amount of 2 parts, *Foeniculum vulgare* in amount of 1 part, *Helichrysum angustifolia* in an amount of 1 part, *Juniperus virginiana* in an amount of 0.5 parts, *Lavendula officinalis* in an amount of 1 part, *Myristica fragrans* in an amount of 2 parts, *Ocimum basilicim* in amount of 2 parts, *Pinus sylvestris* in an amount of 1 part, *Piper nigrum* in an amount of 2 parts, *Rosemarinus officinalis* in an amount of 1 part, *Salvia officinalis lamiacae* in an amount of 1 part, *Salvia sclarea* in an amount of 2 parts and *Zingiber officinale* in an amount of 2 parts.

5. The topical composition of claim 1, wherein said *Calophyllum inophyllum, Citrus aurantium, Eucalyptus globulus, Eugenia caryophyllata, Foeniculum vulgare, Helichrysum angustifolia, Juniperus virginiana, Lavendula officinalis, Myristica fragrans, Ocimum basilicim, Pinus sylvestris, Piper nigrum, Rosemarinus officinalis, Salvia officinalis lamiacae, Salvia sclarea* and *Zingiber officinale* are present in a combined total amount of 20 wt. % of said composition, and wherein said composition further comprises: a stabilizer in an amount of approximately 10 wt %, and a carrier oil in an amount of 70 wt. %.

6. The topical composition of claim 5, wherein said topical composition comprises *Calophyllum inophyllum* in an amount of 1 part, *Citrus aurantium* in an amount of 2 parts, *Eucalyptus globulus* in an amount of 1 part, *Eugenia caryophyllata* in an amount of 2 parts, *Foeniculum vulgare* in amount of 1 part, *Helichrysum angustifolia* in an amount of 1 part, *Juniperus virginiana* in an amount of 0.5 parts, *Lavendula officinalis* in an amount of 1 part, *Myristica fragrans* in an amount of 2 parts, *Ocimum basilicim* in amount of 2 parts, *Pinus sylvestris* in an amount of 1 part, *Piper nigrum* in an amount of 2 parts, *Rosemarinus officinalis* in an amount of 1 part, *Salvia officinalis lamiacae* in an amount of 1 part, *Salvia sclarea* in an amount of 2 parts and *Zingiber officinale* in an amount of 2 parts.

* * * * *